United States Patent [19]

Toyama et al.

[11] Patent Number: 4,894,442
[45] Date of Patent: Jan. 16, 1990

[54] MONOCLONAL ANTIBODIES THAT BIND TO ALPHA$_1$-ACID GLYCOPROTEIN

[75] Inventors: Sakuji Toyama, Kyoto; Masao Tanihara, Kurashiki, both of Japan

[73] Assignee: Kuraray Co., Ltd., Okayama, Japan

[21] Appl. No.: 849,328

[22] Filed: Apr. 8, 1986

[30] Foreign Application Priority Data

Apr. 12, 1985 [JP] Japan ................................. 60-78965

[51] Int. Cl.$^4$ ............................................. C07K 15/00
[52] U.S. Cl. ............................... 530/387; 435/240.27; 435/70.21; 435/172.2; 435/7; 436/548; 935/104; 935/110
[58] Field of Search ............... 530/387, 809, 388, 395; 435/240, 27, 68, 172.2, 7; 935/104, 110, 100, 108; 436/548; 424/85.8, 85.91

[56] References Cited

PUBLICATIONS

Young, W. W. et al., "Production of Monoclonal Antibodies Specific for Two Distinct Steric Portions of the Glycolipid Gauglio—N–Triosylceramide (Asialo GM$_2$)," *J. Exp. Med.*, 150:1008–1019, Oct. 1979.

Ochi, Y. et al. (II), "Immunological Similarity of CEA with $\alpha_1$-Acid Glycoprotein (Orosomucoid)," *Clinica Chemica Acta*, 122:145–160, 1982.

Kupchik, H. Z. et al., "Monoclonal Antibodies to Carcinoembryonic Antigen Produced by Somatic Cell Fusion," *Cancer Research*, 41:3306–3310, Sep., 1981.

Ochi, Y. et al. (I), "Immunochemical Identification of an $\alpha_1$-Acid Glycoprotein–Autigenic Determinant on Carcinoembryonic Antigen (CEA) and Non–Specific Cross-Reacting Antigen (NCA)," *Clinica Chemica Acta*, 138:9–9, 1984.

Federation Proceedings (U.S.), vol. 45, No. 6, p. 1574, (1986).
Clinical Research (U.S.), vol. 33, No. 2, Part 1, p. 193A, (1985).
Clinical Research (U.S.), vol. 33, No. 1, p. 9A, (1985).
Chemical Abstracts 98:51676F, (1983).
Chemical Abstracts 94:203339f, (1981).
Chemical Abstracts 97:90148j, (1982).

*Primary Examiner*—Margaret Moskowitz
*Assistant Examiner*—Kay E. Cheney

[57] ABSTRACT

A monoclonal antibody specific for an $\alpha_1$-acid glycoprotein or for at least one antigenic determinant included in a sugar chain of the following formula:

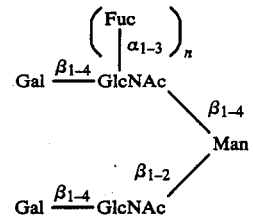

wherein Gal means galactose, GlcNAc means N-acetylglucosamine, Man means mannose, Fuc means fucose, and n is 0 or 1, which is useful for the measurement of glycoproteins in cells, tissues and blood and therefore is useful for diagnosis of various diseases, particularly tumors, and a method for the production thereof by fusing a neoplasm cell line with antibody-producing cells from an animal which has been immunized against an desialylated glycoprotein and culturing the resultant hybridoma.

2 Claims, 3 Drawing Sheets

MONOCLONAL ANTIBODIES THAT BIND TO ALPHA-ACID GLYCOPROTEIN

This invention relates to a monoclonal antibody and a method for the production thereof. More particularly, it relates to a monoclonal antibody specific for a $\alpha_1$-acid glycoprotein or specific for at least one antigenic determinant included in a sugar chain of the following formula which is contained in glycoproteins such as $\alpha_1$-acid glycoprotein:

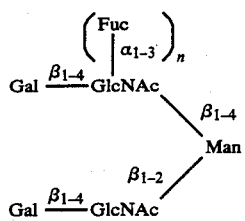

(I)

wherein Gal means galactose, GlcNAc means N-acetylglucosamine, Man means mannose, Fuc mans fucose, and n represents 0 or 1 (hereinafter, this sugar chain is referred to as "sugar chain-I") and a method for the production of the monoclonal antibody. The monoclonal antibody is useful for the measurement of glycoproteins in cells, tissues and blood and therefore useful for diagnosis of various diseases.

PRIOR ART

A monoclonal antibody is usually prepared by fusing antibody-producing cells from a mammal which has been immunized against a particular antigen, with an appropriate neoplasm cell line having unlimited growing properties, for example, a myeloma cell line, and cloning the resultant hybridoma [cf. G Köhler and C. Milstein, Nature, 256, 495 (1975)]. The hybridoma inherits an antibody producing property from the antibody-producing cells and also unlimited growing property from the neoplasm cell line. Each antibody-producing cell can produce an antibody having single specificity (monoclonal antibody), and hence, the hybridoma prepared therefrom can produce the monoclonal antibody in a medium within a flask or in ascites or blood of the host animals. The monoclonal antibody thus prepared has homogeneity and high specificity, and hence, is particularly useful for diagnostic testing.

It has recently become known that the concentration of $\alpha_1$-acid glycoprotein (hereinafter, referred to as "$\alpha_1$-AGP") in cells, tissues or blood has a relation to various diseases such as tumors. For instance, it is known that human $\alpha_1$-AGP is an acute phase reactant having a molecular weight of about 44,000 and the blood level thereof increases in patients suffering from heavy infectious disease or other various diseases. Moreover, it is reported that $\alpha_1$-AGP suppresses an immunoreaction (e.g. lumphocyte blastogenesis, etc.) in vitro [cf. M. Bennet, et al., Proc. Natl. Acad. Sci., USA, 77 (10) 6109 (1980)].

Besides, recent attention has focused on $\alpha_1$-AGP as an immunosuppressive material which is found in blood of patients suffering from tumors, and Ishida et al have reported that a subfraction of $\alpha_1$-AGP having an isoelectric point of about 3.0 was isolated from ascites of a tumor patient, which was named as Immunosuppressive Acidic Protein (abbreviated as "IAP"), and that it could be used as a tumor marker by measuring the IAP level in human blood with an antiserum prepared from a rabbit immunized thereby [cf. K. Tamura, et al., Cancer Res., 41, 3244 (1982)]. Although this IAP isolated by Ishida et al. is usually used as a tumor marker which is non-specific for organs, the anti-IAP antiserum used in the test is a mixture of various antibodies having various specificities (polyclonal antibody) and does not have high specificity. Furthermore, this IAP has also the problem that antibody titer or specificity of the antiserum varies depending on the individual animal to be immunized. In the diagnosis of tumors, attention has also focused on monoclonal antibodies, but never before on a monoclonal antibody specific for $\alpha_1$-AGP or specific for sugar chain-I.

BRIEF SUMMARY OF THE INVENTION

The present inventors have searched for an monoclonal antibody specific for $\alpha_1$-AGP or for at least one antigenic determinant included in the sugar chain-I and found that when a hybridoma is prepared by using cells of an animal immunized merely against $\alpha_1$-AGP or a glycoprotein containing sugar chain-I, the desired monoclonal antibody cannot be obtained, but when the terminal sialic acid moiety of sugar chain in $\alpha_1$-AGP or glycoproteins containing the sugar chain-I is deleted, such de-sialylated glycoproteins show high immunogenicity, and hence, by fusing a neoplasm cell line with cells of animals immunized against the desialylated glycoproteins, a hybridoma can be obtained which can produce the desired monoclonal antibody specific for $\alpha_1$-AGP or for at least one antigenic determinant included in the sugar chain-I.

An object of the invention is to provide a monoclonal antibody specific for $\alpha_1$-AGP or for at least one antigenic determinant included in the sugar chain-I. Another object of the invention is to provide a method for producing a monoclonal antibody specific for $\alpha_1$-AGP or for at least one antigenic determinant included in the sugar chain-I by fusing a neoplasm cell line with antibody producing cells from an animal which has been immunized against a desialylated glycoprotein and culturing the resultant hybridoma. These and other objects and advantages of the invention will be apparent to persons skilled in the art from the following description.

BRIEF DESCRIPTION OF THE DRAWING

The accompanying

DETAILED DESCRIPTION OF THE INVENTION

Figure 1:
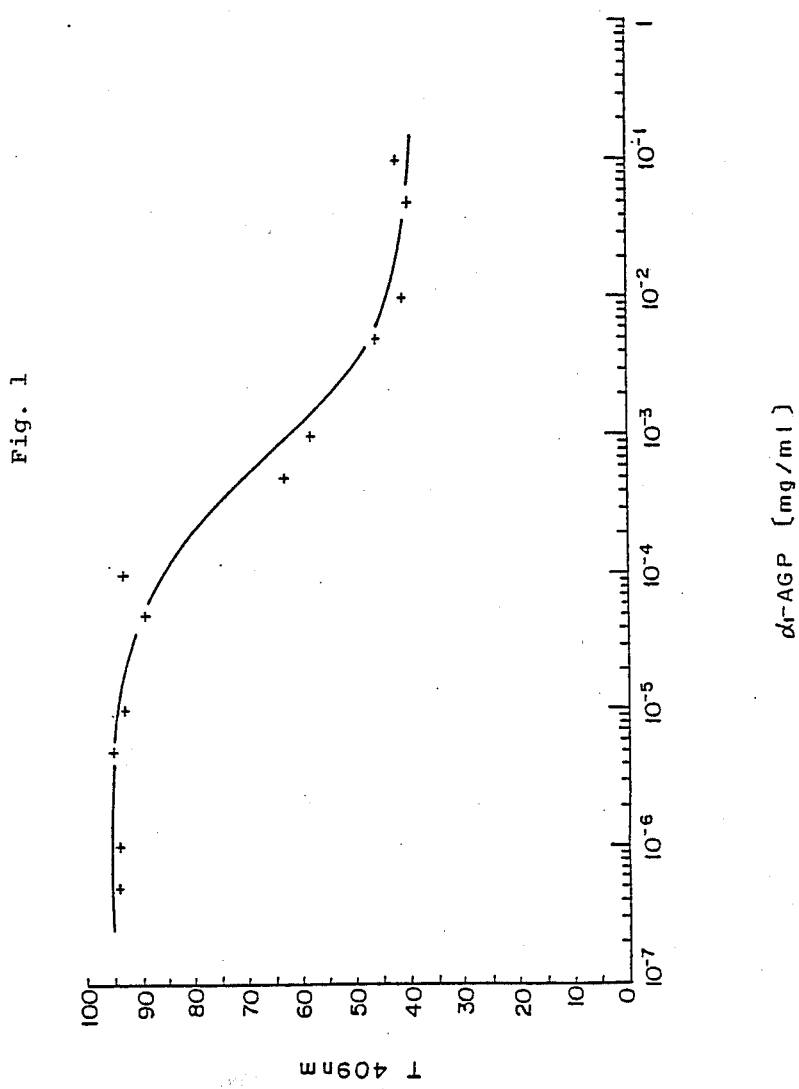
FIG. 1 shows a calibration curve by ELISA (enzyme-linked immunosorbent assay) wherein a monoclonal antibody, HA-7 of this invention was immobilized.

In the present invention, animals are immunized against $\alpha_1$-AGP or glycoproteins containing sugar chain-I which has been subjected to a treatment for deletion of sialic acid. The glycoproteins containing sugar chain-I include $\alpha_1$-AGP, fetuin, ceruloplasmin, CEA (carcino embryonic antigen), and the like. Among these glycoproteins, a presence of the sugar chain both with a fucose (n=1 in the formula I) and without a fucose (n=0 in the formula I) has been reported for $\alpha_1$-AGP, ceruloplasmin and CEA. A presence of the sugar chain with a fucose (n=1 in the formula I) has not been reported for fetuin.

The deletion of sialic acid from $\alpha_1$-AGP and other glycoproteins can be carried by conventional methods, for example, hydrolysis with an enzyme (e.g. sialidase), or hydrolysis with an acid. The enzyme for the deletion of sialic acid is preferably free from protease and highly pure. Impure sialidase usually includes protease and hence disadvantageously hydrolyzes not only sialic acid but also peptide chain. The hydrolysis with an acid should be done as much as possible under conditions such that any peptide chain is not hydrolyzed but sialic acid is deleted. For example, it can be done by treating the glycoproteins with a diluted mineral acid (e.g. diluted sulfuric acid) under heating at a temperature of about 80° C. for several hours.

Immunization of the animal is carried out by injecting an emulsion mixture of the de-sialylated glycoprotein with Freund's complete adjuvant. The Freund's complete adjuvant is admixed in order to assure the immunization, and other conventional means are also usable.

The animals to the immunized include various animals, but preferably are mice and rats, from which there are obtained many neoplasm cells suitable as a partner of the hybridoma, in particular, BALB/c mouse from which many neoplasm cells are available.

The antibody-producing cells are most preferably spleen cells of the above BALB/c mouse, but may be other animal cells, such as spleen cells of rats, lymphocytes of rabbits, lymphocytes of sheep, and the like.

The neoplasm cells may be any cells which can give unlimited growing property to the hybridoma, but are preferably myeloma cells. Suitable examples of the myeloma cell lines are $P_3$-X63-Ag8 [cf. Nature, 256, 495 (1975)], $P_3$-X63-Ag8-653 [ATCC number: CRL-1580, cf. J. Immunol., 123, 1548 (1979)], $P_3$-NSI/1-Ag4-1 [cf. Eur. J. Immunol., 6, 511 (1976)], S194, Y3, SP2/O [ATCC number: CRT-1581, cf. Nature, 276, 269 (1978)], MPC-11 [ATCC number: CCL-167, cf. J. Exp. Med., 131, 515 (1970)], and mutants of these cells. These cells lack nucleic acid producibility by salvage pathway and are preferable also in view of selection of suitable hybridoma as mentioned hereinafter. Among the above-mentioned cell lines, $P_3$-NSI/1-Ag4-1 has a high growth rate and a high antibody producing capacity and hence is preferably used.

The fusion of the antibody-producing cells and the neoplasm cells can be done by a known technique, for instance, by using HVJ [Hemagglutinin Virus of Japan, other name: Sendai virus, cf. Yoshio Okada, "Cell fusion and Cell Engineering" issued by Kodansha, page 19 (1975)] or polyethylene glycol [cf. V. T. Ohi, L. A. Herzenberg, "Selected Method in Cellular Immunology" edd. by B. B. Michell, issued by W. H. Freeman, Chapter 17] or by electric fusion, or the like.

The mouse myeloma cells as mentioned above lack the nucleic acid producibility by salvage pathway, and hence can synthesize nucleic acid only by de novo pathway. On the other hand, the hybridoma cell line has a nucleic acid producibility by salvage pathway origined from the antibody-producing cells and hence can selectively be grown in a hypoxanthine-aminopterine-thymidine (HAT) medium (usually, RPMI-1640 medium supplemented with 10–15% fetal calf serum (FCS).

The production by the hybridoma of a monoclonal antibody specific for glycoproteins can be confirmed by agglutination reaction using sheep erythrocytes which are bound with de-sialylated glycoprotein or untreated glycoprotein. It can also be confirmed by an enzyme linked immunosorbent assay (ELISA) using an immobilized glycoprotein which is de-sialylated or untreated.

The hybridoma which produces a monoclonal antibody specific for glycoproteins is cloned by a method of limiting dilution.

The hybrodoma cell line thus obtained can be grown in vitro on a suitable medium (usually, RPMI-1640 medium supplemented with 10–15% FCS) while producing the desired antibody. The hybridoma cell line may also be cultured within the body of the same animal as that from which the neoplasm cells used for the cell fusion are obtained, by which the desired monoclonal antibody can be produced in the ascites and blood in high concentrations.

The monoclonal antibody may be used for the detection of glycoproteins in cells or sera in the form of a culture supernatant or ascites or serum, but it may be purified by a conventional purification method, such as salting out with ammonium sulfate, ion exchange chromatography, affinity chromatography, and the like. The purified antibody may be used as it is, or after being labelled with radioisotope, fluorescence, enzyme, biotin, etc.

The detection can be carried out by known techniques, such as radioimmunoassay, fluorescence immunoassay, enzyme immunoassay, agglutination, and the like. Detection of glycoproteins in serum is preferably carried out by agglutination, radioimmunoassay, or enzyme immunoassay. Detection of glycoproteins in cells and tissues is preferably carried out by fluorescence immunoassay and enzyme immunoassay. The monoclonal antibody of this invention is not limited to these usages.

The monoclonal antibody of this invention is useful for the detection of glycoproteins in cells, tissues and blood and hence for diagnosis of various diseases, particularly diagnosis of tumors.

The present invention is illustrated by the following Example and Reference Example.

EXAMPLE (1) Preparation of de-sialylated $\alpha_1$-AGP by treatment with sulfuric acid Purified $\alpha_1$-AGP was obtained from pooled human sera by a known method [cf. W. Burgi and K. Schmid, J. Biol. Chem, 236, 1066 (1961)]. The $\alpha_1$-AGP (10 mg) was dissolved in 0.1N sulfuric acid (10 ml), and the mixture was stirred at 80° C. for 1 hour. After cooling, the reaction mixture was neutralized with 3N aqueous NaOH solution, and then dialyzed against water at 4° C. The resultant was lyophilized to give de-sialylated $\alpha_1$-AGP (about 4 mg).

(2) Preparation of de-sialylated fetuin by treatment with sulfuric acid:

A commercially available fetuin (Type IV, manufactured by Sigma Co., purified product obtained from fetal calf serum) was treated in the same manner as described above in (1) to give a de-sialylated fetuin.

(3)-(a) Preparation of de-sialylated $\alpha_1$-AGP by treatment with enzyme:

The same $\alpha_1$-AGP (10 mg) as used above (1) was dissolved in PBS (phosphate buffered saline, pH 7.4) (10 ml), and thereto was added sialidase [E.C.3.2.1.18] (0.25 unit), and the mixture was stirred at 37° C. for 30 minutes. The reaction mixture was dialyzed against water at 4° C. and then lyophilized to give a di-sialylated $\alpha_1$-AGP (about 4 mg).

(3)-(b) Preparation of the de-sialylated ceruloplasmin by treatment with enzyme:

A commercially available ceruloplasmin (manufactured by Green-Cross Co., Japan) was treated in the same manner as described above in (3)-(a) to give desialylated ceruloplasmin.

(4) Preparation of antibody producing cells:

The de-sialylated $\alpha_1$-AGP obtained above in (1) was dissolved in physiological saline solution, sterilized by filtration, mixed with Freund's complete adjuvant, and the mixture was injected intraperitoneally into a mouse (BALB/c) in an amount of de-sialylated $\alpha_1$-AGP: 500 μg/mouse, by which the mouse was immunized. After 3 weeks, the mouse was given a booster injection with a mixture of an aqueous aluminum phosphate solution and a physiological saline solution of the desialylated $\alpha_1$-AGP in the same amount as above.

On the third day after the booster injection, the spleen cells were taken out and were used as antibody producing cells for the following example.

(5) Cell fusion:

The antibody producing cells ($6.5 \times 10^8$ cells) were fused with neoplasm cells (P$_3$-NNSI/1-Ag4-1) ($3.3 \times 10^8$ cells) by polyethylene glycol (PEG#1500). The fused cells were cultured in HAT medium (HAT-containing RPMI-1640 medium supplemented with 15% FCS) to grow selectively only the hybridoma. About 10 days after the cell fusion. The specific antibody was checked by agglutination test using an antigen-sensitized sheep erythrocyte. The specific antibody producing hybridoma was cloned by limiting dilution, and then, there were selected 5 hybridoma cell lines which produced monoclonal antibody specific for $\alpha_1$-AGP (these cell lines and the monoclonal antibodies produced from each cell line are designated as HA-2, HA-3, HA-5, HA-7 and HA-10, respectively) and one hybridoma cell line which produced monoclonal antibody specific for an antigenic determinant included in the sugar chain-I (the cell line and the monoclonal antibody produced from the cell line are designated as HA-13). These hybridoma cell lines were unlimitedly grown in vitro (in RPMI-1640 medium supplemented with 15% FCS) and also within the peritoneal cavity of a BALB/c mouse and hence the desired monoclonal antibody could be obtained from the culture supernatant or the ascites.

(6) Detection of specificity of antibody by Western blotting:

(i) Hybridoma cell lines, HA-2, HA-3, HA-5, HA-7 and HA-10: $\alpha_1$-AGP, de-sialated $\alpha_1$-AGP and human serum were subjected to an electrophoresis with sodium laurylsulfatepolyacrylamide gel (SDS-PAGE, gel concentration 10%), and thereafter, an electric blotting was carried out from the gel to a nylon membrane (Zeta-Probe, manufactured by Bio-Rad Co.).

The nylon membrane was treated was 10% sheep serum-containing PBS and then reacted with a culture supernatant of a hybridoma cell line which produced anti-$\alpha_1$-AGP monoclonal antibody, and further reacted with a horse radish peroxidase (HRP)-anti-mouse Ig antibody, and thereafter, the reaction mixture was specifically stained by diaminobenzidine in the presence of $H_2O_2$.

By the above test, in the culture supernatant of all of the hybridoma cell lines in this invention, only the band of $\alpha_1$-ADP (untreated and de-sialylated) was specifically stained, by which it was confirmed that the monoclonal antibody of this invention can specifically react only with $\alpha_1$-AGP.

(ii) Hybridoma cell line HA-13: $\alpha_1$-AGP, de-sialylated $\alpha_1$-AGP, fetuin, de-sialated fetuin, ceruloplasmin, and de-sialylated ceruloplasmin were subjected to an electrophoresis with sodium laurylsulfatepolyacrylamide gel (SDS-PAGE, gel concentration 10%), and thereafter, an electric blotting was carried out from the gel to a nylon membrane (Zeta-Probe, manufactured by Bio-Rad Co.).

The nylon membrane was treated with 10% sheep serum-containing PBS and then reacted with a culture supernatant of a hybridoma cell line (HA-13) which produced anti-sugar chain-I monoclonal antibody and further reacted with a horse radish peroxidase (HRP)-anti-mouse Ig antibody, and thereafter, the reaction mixture was specifically stained by diaminobenzidine in the presence of $H_2O_2$.

By the above test, the de-sialylated $\alpha_1$-AGP, desialated fetuin, and de-sialylated ceruloplasmin were specifically stained, but untreated $\alpha_1$-AGP, untreated fetuin and untreated ceruloplasmin were not stained, by which it was confirmed that HA-13 was specifically reacted with at least one antigenic determinant included in the sugar chain-I common to the glycoproteins.

(7) Characteristics of the monoclonal antibody and purification thereof:

(i) Class of the antibody: It was confirmed that the immunoglobulins produced by the hybridoma cell lines of this invention are IgG$_1$ (HA-3, HA-7, HA-10) and IgM (HA-2, HA-5, HA-13), respectively, by Ouchterlony method [cf. O, Ouchterlony, Prog. Allergy, 5, 1 (1958)].

(ii) Purification by salting out with ammonium sulfate: The culture supernatants or ascites obtained by culturing of the hybridoma cell lines were subjected to precipitation by saturation with 50% ammonium sulfate, which was repeated twice, and thereafter, the precipitates were dialyzed against water at 4° C. and lyophilized to give monoclonal antibody Ig fraction.

(iii) Purification by affinity chromatography: The culture supernatants or ascites obtained by culturing of the hybridoma cell lines of this invention were subjected to purification as they stand, or after being specifically bound with a de-sialylated $\alpha_1$-AGP - Sepharose [which was prepared from CNBr-Sepharose (manufactured by Pharmacia, Sweden) and de-sialylated $\alpha_1$-AGP by a known method], followed by eluting the bound monoclonal antibody with a glycine-HCl buffer (pH 2.5) and then neutralizing. The solution was dialyzed against water at 4° C., and lyophilized to give affinity-purified monoclonal antibodies.

(8) Detection of $\alpha_1$-AGP and an antigenic determinant included in the sugar chain-I in serum:

(i) Preparation of a monoclonal antibody bound with biotin: The affinity-purified monoclonal antibody (2 mg) obtained above was dissolved in 0.1 mM aqueous NaHCO$_3$ solution (2 ml) and thereto was added a solution (200 μl) of NHS-biotin (manufactured by Pierce Bo.) (1 mg/ml) in dimethylformamide (DMF), and the mixture was reacted at room temperature for 4 hours.

The reaction mixture was dialyzed against PBS at 4° C. to give a monoclonal antibody bound with biotin.

(ii) Detection of $\alpha_1$-AGP in serum by ELISA method-1: A PBS solution of affinity-purified monoclonal antibody (0.05 mg/ml) was placed on a Falcon 3912 microtest plate in an amount of 50 µl/well, and allowed to stand at room temperature overnight in order to immobilize the antibody. Thereafter, 5% FCS-containing PBS was added thereto in an amount of 300 µl/well, and allowed to stand 37° C. for 2 hours, by which non-specific adsorption site was blocked. A serum to be tested and a 5% FCS-containing PBS solution of a known amount of $\alpha_1$-ACP (for calibration) were each added in an amount of 25 µl/well, and the combination was allowed to stand at 37° C. for 1 hour. A 5% FCS-containing PBS solution of IgC fraction of rabbit anti-$\alpha_1$-AGP antiserum (manufactured by Dako Co.) (0.01 mg/ml) was added in an amount of 50 µl/well, and it was allowed to stand at 37° C. for 1 hour. Furthermore, 5% FCS-containing PBS solution (0.002 mg/ml) of HRP-labelled anti-rabbit IgC-antiserum (manufactured by Amersham) was added in an amount of 50 µl/well, and it was allowed to stand at 37° C. for 1 hour. The resultant was reacted with 1 mM 2,2'-azino-bis(3-ethylbenzothiazoline-6sulfonic acid (ABTS) in the presence of $H_2O_2$, and a transmission at 409 nm was measured.

From the transmission in a well added with an $\alpha_1$-AGP of a known concentration and the concentration thereof, a calibration curve was drawn. Based upon the calibration curve, the concentration of $\alpha_1$-AGP in the test serum was calculated.

An example of the calibration curve obtained by using HA-7 in the above procedure is shown in the accompanying FIG. 1.

In the case of HA-7, the concentration of $\alpha_1$-AGP was 1.1±0.1 (S.E.) µg/ml in normal subjects (N=10) and 2.2±0.7 (S.E.) µg/ml in tumor patients (N=13). Thus, it is clear that the $\alpha_1$-AGP concentration in serum of the tumor patients was higher than that of the normal subjects and because of varying of the data depending on the state of disease, the data were widely distributed.

(iii) Detection of $\alpha_1$-AGP in serum by ELISA method-2: A PBS solution of an IgG fraction of a rabbit anti-$\alpha_1$-AGP anti-serum (manufactured by Dako Co.) (0.1 mg/ml) was immobilized on a plate in the same manner as described above in (8)-(ii).

In the same manner as in the above (8)-(ii), the non-specific adsorption site was blocked, and thereto were added a test serum and $\alpha_1$-AGP having a known concentration. Thereafter, a 5% FCS-containing PBS solution of biotin-conjugated monoclonal antibody (0.005 mg/ml) prepared in (8)-(i) and further a Tris buffered saline solution (TBS) (pH 7.4) of HRP-labelled avidine (manufactured by Vector Co.) were added thereto, and the combination was reacted at 37° C. for 15 minutes and then with ABTS like in (8)-(ii).

By the above method, a similar calibration curve to FIG. 1 was obtained. Based on the calibration curve, the $\alpha_1$-AGP concentration in the test serum was calculated. As a result, in case of HA-2, the concentration of $\alpha_1$-AGP was 1.68±0.50 (S.E.) µg/ml in normal subjects (N=10) and 1.58±0.73 (S.E.) µg/ml in tumor patients. It was difficult to distinguish in respect to HA-2 between the normal subjects and the tumor patients, but $\alpha_1$-AGP in serum could clearly be detected.

(iv) Detection of $\alpha_1$-AGP in serum by ELISA method-3: In the same manner as described in (8)-(ii), an affinity-purified monoclonal antibody was immobilized onto a plate, the non-specific adsorption site was blocked, and the test serum and an $\alpha_1$-AGP having a known concentration were reacted. Thereto was added biotin-conjugated monoclonal antibody, HRP-labelled avidine was bound and the combination was reacted with ABTS like in (8)-(iii). A calibration curve was drawn and based on the calibration curve, the $\alpha_1$-AGP concentration in test serum was calculated.

Figure 2:
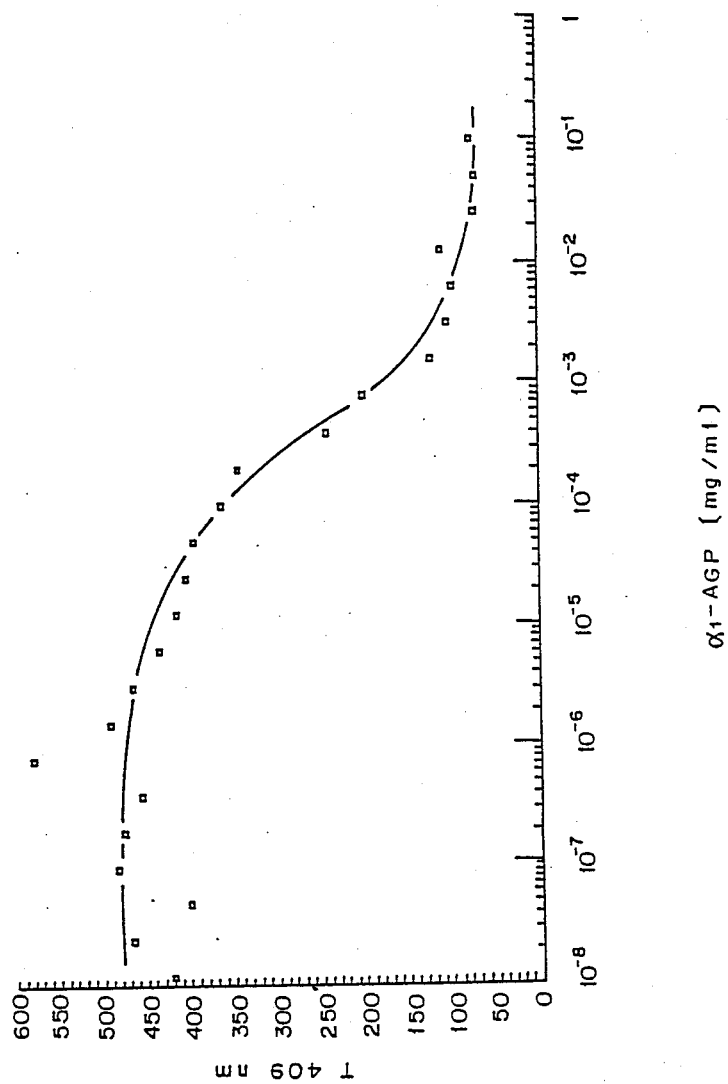
FIG. 2 shows a calibration curve by ELISA wherein a monochlonal antibody, HA-7 of this invention was immobilized and biotin-conjugated HA-5 was further reacted.

The accompanying FIG. 2 shows a calibration curve obtained in the case of immobilized of HA-7, followed by reacting with biotin-conjugated HA-5. By the result of the test, in the case of using HA-7 and biotin-conjugated HA-5, the concentration of $\alpha_1$-AGP was 0.37±0.04 (S.E.) µg/ml in normal subjects (N=10) and 0.84±0.16 (S.E.) µg/ml in tumor patients (N=13).

(v) Detection of an antigenic determinant included in the sugar chain-I in serum by ELISA method: A PBS solution of affinity-purified monoclonal antibody (HA-13, 0.05 mg/ml) was poured onto Falcon 3912 microtest plate in an amount of each 50 µl/well, and the plate was allowed to stand at room temperature overnight to immobilize the antibody. Thereto was added 5% FCS-containing PBS in an amount of 300 µl/well, and it was allowed to stand at 37° C. for 2 hours, by which the non-specific adsorption site was blocked. Thereto were added a test serum and a 5% FCScontaining PBS solution of de-sialylated $\alpha_1$-AGP having a known concentration in an amount of 25 µl/well, and the combination was allowed to stand 37° C. for 1 hour. A 5% FCS containing PBS solution of biotin-conjugated monoclonal antibody (biotin-HA-13) (0.002 mg/ml) prepared above in (8)-(i) was added thereto, and further a TBS solution (Tris buffered saline solution, pH 7.4) of HRP-labelled avidine (manufactured by Vector Co.) (0.002 mg/ml) was added, and the combination was reacted at 37° C. for 15 minutes. Thereafter, it was reacted with 1 mM ABTS in the presence of $H_2O_2$, and a transmission at 409 nm was measured.

From the transmission of a well to which was added di-sialylated $\alpha_1$-AGP having a known concentration and concentration thereof, a calibration curve was drawn, and based on the calibration curve, the relative concentration of an antigenic determinant included in the sugar chain-I in the test serum was calculated.

Figure 3:
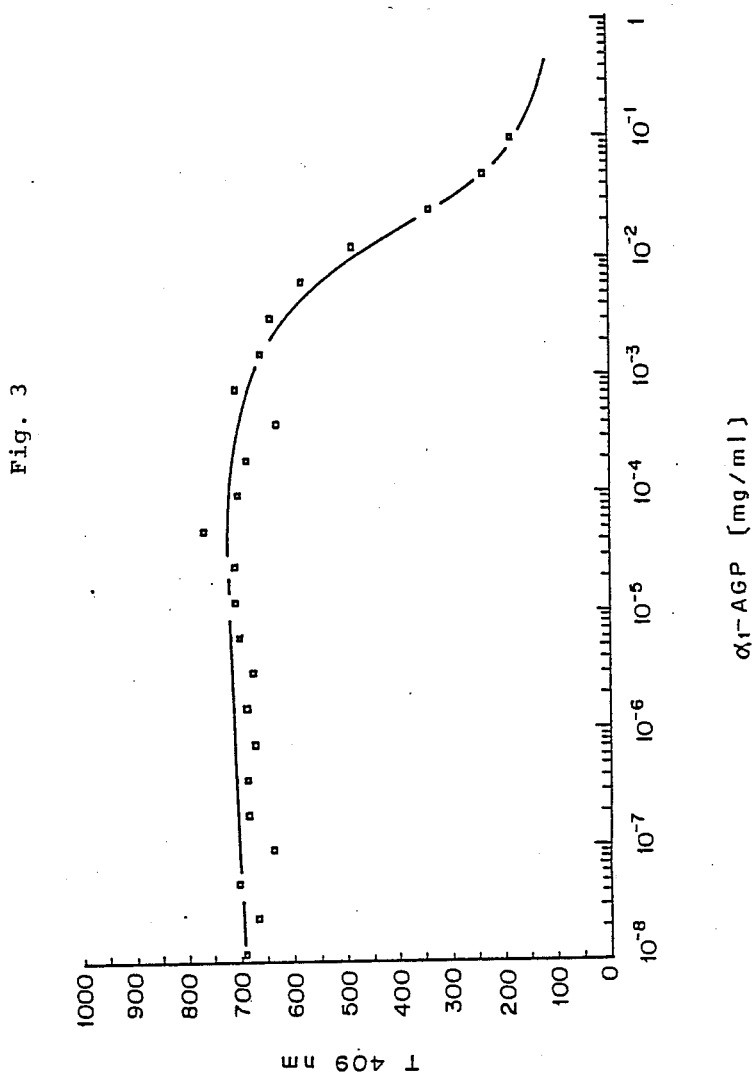
FIG. 3 shows a calibration curve by ELISA wherein a monoclonal antibody, HA-13 of this invention was immobilized and biotin-conjugated HA-13 was further reacted.

One example of the calibration curve in this case is shown in the accompanying FIG. 3. The relative concentration of an antigenic determinant included in the sugar chain-I in serum was 12.2.±3.4 (S.E.) µg/ml in normal subjects (N=10) and 4.8±1.4 (S.E.) µg/ml in tumor patients (N=13). Thus, it is clear that the serum of the tumor patients showed lower concentration of an antigenic determinant included in the sugar chain-I than that of thee normal subjects, and hence, the abnormal glycometabolism in tumor patients can be detected.

(9) Detection of $\alpha_1$-AGP and an antigenic determinant included in the sugar chain-I in cells:

Human lymphocytes ($10^6$ cells) were centrifuged (1,200 r.p.m., 5 minutes), washed with PBS, and thereto was added a PBS solution (5 ml) of biotin-conjugated monoclonal antibody (5 µg/ml) as prepared in (7)-(i), and it was reacted at 4° C. for 2 hours. Then, a NaHCO$_3$ buffered saline solution (pH 8.2) (0.25 ml) of a fluorescein-labelled avidine (manufactured by Vector Co.) (5 µg/ml) was added, and it was reacted at 4° C. for 30 minutes. The reaction mixture was washed with an ice-cooled PBS and then dispersed in a 50% glycerin/PBS, and it was observed with a fluorescent microscope. As a result, there was specifically observed a fluorescence of fluorescein on the cell membrane of the specific lymphocytes.

(10) Detection of $\alpha_1$-AGP and an antigenic determinant included in the sugar chain-I in tissues:

A tissue to be stained was fixed with Bouin solution or Carnoy solution, dehydrated and then embedded with paraffin. The paraffin-embedded tissue was cut in thin sections with a microtome and attached onto a slide glass. Paraffin was removed off with xylene-alcohol subsequently, and the tissue was washed by dipping in PBS for 10 minutes. In case of a freshly frozen section, it was fixed with acetone at $-20°$ C. and then immediately washed with PBS.

A 50% sheep serum-containing PBS was reacted with the tissue section prepared above at room temperature for 30 minutes, by which the non-specific binding site was blocked. The tissue thus reacted was further reacted with a 1% sheep serum-containing PBS solution of a monoclonal antibody purified in the same manner as described in (7) (5-25 $\mu$g/ml) or with a culture supernatent of monoclonal antibodyproducing cells at room temperature for 1 hour. The resultant was washed by dipping in PBS for 10 minutes, and then reacted with a 50% sheep serum-containing PBS solution of an HRP-labelled sheep anti-mouse IgG antibody (10-25 $\mu$g/ml), which had been adsorbed with human serum, at room temperature for 30 minutes. Moreover, after washing by dipping in PBS for 10 minutes, the tissue section thus reacted was specifically stained by diaminobenzidine in the presence of $H_2O_2$. After washing by dipping in PBS for 10 minutes, the tissue was further subjected to a counter-stain with methylene blue. The stained tissue was washed with water, dehydrated with alcohol-xylene subsequently and then mounted with a commercially available mounting agent, and it was observed with a microscope.

Examples of the stained tissues as above are as follows:

In case of HA-2 and HA-5, cytoplasm of epithelial cells in stomach, bile-bladder, gullet, etc., and liver cells were mainly stained, from which it is clear that $\alpha_1$-AGP is distributed within the cytoplasm of these tissues. In case of HA-13, the epithelioglandular Brush border of these tissues was specifically stained, from which it is clear that an antigenic determinant included in the sugar chain-I is specifically distributed within this region. In case of HA-7, the tumor cells of mastocarcinoma tissue were stained in two patients (among five patients), but in the remaining three patients suffering from benign mastedenoma, it was entirely not stained. Besides, in patients suffering from renal cancer, ovarian cancer and uterus cancer, the tissues were stained, but the tissues of gastrointestinal cancer, lung cancer and thyrophyma were entirely not stained. Thus, HA-7 can be used for staining specifically a specific tumor tissue, and hence it is useful for diagnosis of tumors.

Reference Example

Mice were immunized with an untreated $\alpha_1$-AGP in the same manner as described in the above (4), and the antibody-producing cells were taken out.

The antibody-producing cells ($2.5 \times 10^8$ cells) were fused with neoplasm cells (P$_3$-NSI/1-Ag4-1) ($1.1 \times 10^8$ cells) in the same manner as described in the above (5), and there was determined the presence of specific antibody in the culture supernatant of the resulting hybridoma by an enzyme immunoassay using immobilized $\alpha_1$-AGP, In all of 348 wells (100%) poured with the cells, the hybridoma was grown, among which antibody production was observed in 25 wells (7%) by enzyme immunoassay. However, 10 of these hybridoma disappeared the antibody value before cloning step.

Colonies obtained from 15 strains cloned by limiting dilution showed no antibody titer by the enzyme immunoassay. Thus, it is difficult to obtain a stable anti-body-producing hybridoma cell line when the animal is immunized with an untreated $\alpha_1$-AGP.

Hybridoma cell lines HA-5, HA-7 and HA-13 were deposited on June 13, 1989 under the terms of the Budapest Treaty with the Fermentation Research Institute, Agency of Industrial Science and Technology, 1-3, Higashi 1-chome, Yatabe-machi, Tsukuba-gun, Ibaraki-ken, 305, JAPAN; and have been respectively assigned Accession Numbers FERM BP-2470, FERM BP-2471, and FERM BP-2469. The hybridoma cell lines HA-5, HA-7, and HA-13 will be irrevocably and without restriction of condition released to the public upon the issuance of a patent.

What is claimed is:

1. A monoclonal antibody specific for $\alpha_1$-acid glycoprotein, which is selected from the group consisting of HA-5 and HA-7.

2. A monoclonal antibody having all the identifying characteristics of HA-13.

* * * * *